United States Patent
Glenn

(10) Patent No.: US 8,043,247 B1
(45) Date of Patent: *Oct. 25, 2011

(54) SUBARACHNOID EPIDURAL SHUNT

(76) Inventor: Bradley J. Glenn, Oneida, WI (US)

( * ) Notice: Subject to any disclaimer, the term of this patent is extended or adjusted under 35 U.S.C. 154(b) by 368 days.

This patent is subject to a terminal disclaimer.

(21) Appl. No.: 12/384,570

(22) Filed: Apr. 6, 2009

Related U.S. Application Data

(63) Continuation of application No. 11/277,155, filed on Mar. 22, 2006, now Pat. No. 7,513,883.

(51) Int. Cl.
*A61M 5/00* (2006.01)
(52) U.S. Cl. .................................. 604/8; 604/9
(58) Field of Classification Search ............... 604/7–10, 604/264
See application file for complete search history.

(56) References Cited

U.S. PATENT DOCUMENTS

| | | | |
|---|---|---|---|
| 3,298,372 A | 1/1967 | Feinberg |
| 3,889,687 A | 6/1975 | Harris |
| 3,924,635 A | 12/1975 | Hakim |
| 4,413,985 A | 11/1983 | Wellner |
| 4,631,051 A | 12/1986 | Harris |
| 5,643,195 A | 7/1997 | Drevet |
| 6,264,625 B1 | 7/2001 | Rubenstein |
| 6,758,832 B2 | 7/2004 | Barbut |
| 7,004,966 B2 | 2/2006 | Edwin |
| 2002/0183680 A1 | 12/2002 | Kuth |
| 2003/0004495 A1 | 1/2003 | Saul |
| 2003/0032915 A1 | 2/2003 | Saul |
| 2003/0220604 A1 | 11/2003 | Al-Anazi |

FOREIGN PATENT DOCUMENTS

EP  0 873 762  10/1998

OTHER PUBLICATIONS

Salomon Hakim, M.D., Alejandro Jimenez, M.D. and Fernando Rosas, M.D.; Drainage of the Cerebrospinal Fluid into the Spinal Epidural Space: a New Technique for the Treatment of Hydrocephalus; Acta Neurochirurgica; vol. 4, No. 3; Sep. 1955; pp. 224-227.

*Primary Examiner* — Leslie Deak
(74) *Attorney, Agent, or Firm* — Heisler & Associates

(57) ABSTRACT

Methods and devices are provided for shunting fluid to treat hydrocephalous, and in particular for treating normal pressure hydrocephalous, or Alzheimer's, Idiopathic Intracranial Hypertension (IIH), or any other condition in which it is necessary to drain and/or cleanse CSF. The methods and devices utilize a shunt having an inlet port, and outlet port, and a flow control component for controlling fluid flow from the inlet port to the outlet port. The shunt can be implanted at a location along or within a patient's spinal column. In one exemplary embodiment, an inlet port of a shunt can be implanted within the subarachnoid space, and an outlet port of a shunt can be implanted at a drainage site. In certain exemplary embodiments, the cerebrospinal fluid is drained into the epidural space.

30 Claims, 14 Drawing Sheets

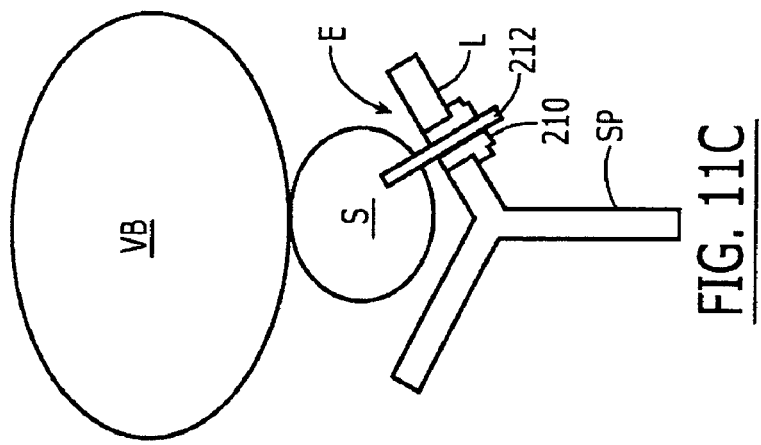
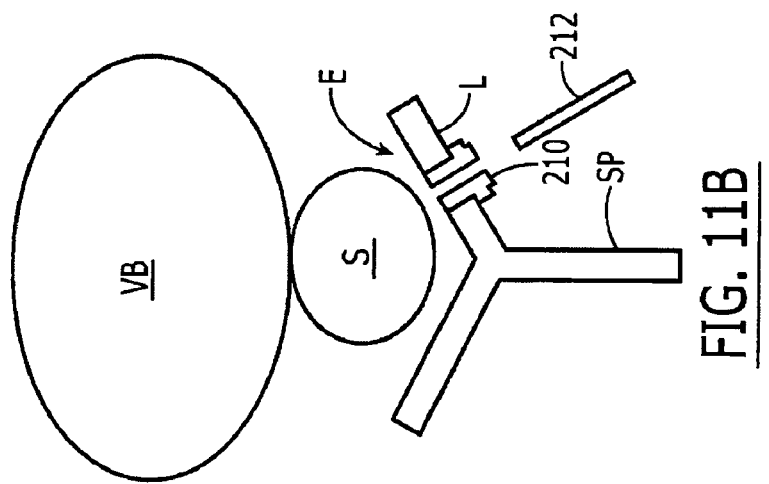
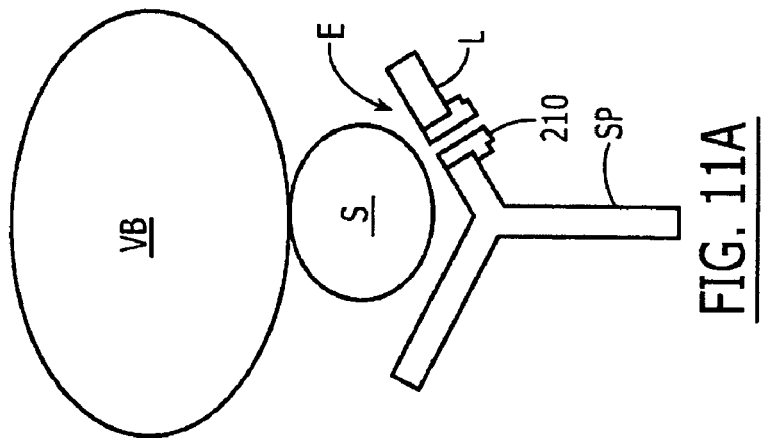

SUBARACHNOID EPIDURAL SHUNT

CROSS-REFERENCE TO RELATED APPLICATIONS

This application is a continuation of U.S. patent application Ser. No. 11/277,155, filed on Mar. 22, 2006 (now U.S. Pat. No. 7,513,883).

FIELD OF THE INVENTION

The present invention relates to methods and devices for shunting cerebrospinal fluid.

BACKGROUND OF THE INVENTION

Many conditions benefit from shunting, removal, or cleansing of CSF, including hydrocephalus, pseudotumor cerebri (Idiopathic Intracranial Hypertension, IIH), and Alzheimer's disease. Hydrocephalus, for example, is a condition afflicting patients who are unable to regulate cerebrospinal fluid flow through their body's own natural pathways. Produced by the ventricular system, cerebrospinal fluid (CSF) is normally absorbed by the body's venous system. In a patient suffering from hydrocephalus, the cerebrospinal fluid is not absorbed in this manner, but instead accumulates in the ventricles of the patient's brain and can lead to serious medical conditions.

Hydrocephalus exists in two forms: communicating (non-obstructive hydrocephalus) caused by inadequate absorption of CSF when the ventricular pathways are not obstructed; and non-communicating (obstructive hydrocephalus) caused by blockage in the ventricular pathways through which CSF flows. Hydrocephalus can also be either congenital, where the condition is present at birth or detected soon thereafter, or acquired, where the condition is acquired as the result of infection, head trauma, brain tumors, cysts, etc. Normal pressure hydrocephalus (NPH) is a type of communicating (non-obstructive) hydrocephalous that occurs in adults, usually older adults. The drainage of CSF is blocked gradually, and the excess fluid builds up slowly. With NPH it is believed that the ventricles enlarge to handle the increased volume of the CSF, and the compression of the brain from within by the fluid-filled ventricles destroys or damages brain tissue causing some of the symptoms. Unlike other types of Hydrocephalus that typically result in increased pressure in the head when too much CSF accumulates, NPH shows little to no increased pressure, thus leading to the name "Normal Pressure Hydrocephalus."

NPH can be treated by draining the excess fluid from the ventricular system to another area of the patient's body, such as the abdomen or vascular system, where it can be reabsorbed into the bloodstream. A drainage system, commonly referred to as a shunt, is often used to carry out the transfer of fluid. It consists of a system of catheters with a flow control component to control fluid drainage and prevent back-flow. In order to install the shunt, typically a scalp incision is made and a small hole is drilled in the skull. Current shunts used to treat NPH are inserted surgically so that the upper end is in communication with the ventricular system. Since NPH is non-obstructive, the upper end or proximal catheter of the shunt can be placed either in the ventricles (ventricular catheter) or in the sub-arachnoid space at the level of the lumbar spinal column (lumbar catheter). The lower end or distal catheter of the shunt can lead into the abdomen (ventriculoperitoneal shunt), wherein it passes into the bloodstream. There are several other body cavities available for distal drainage of a shunt. When shunts were first introduced, a one-way valve drained spinal fluid directly into the right atrium of the heart via the jugular vein (ventriculoatrial shunt). Vascular shunts functioned very well, but they were prone to multiple problems including early and late infection, as well as rare, potentially fatal heart failure due to blockage of blood vessels within the lungs by particles of blood clot flaking off the shunt's catheter tip. The use of the heart has been largely abandoned as an initial choice because of these problems but it remains a viable second option when infection or surgery has rendered the abdominal cavity unaccommodating of the distal shunt catheter. The chest cavity is another cavity which can be used as a backup to the abdominal cavity (ventriculopleural shunt). The catheter is placed inside the rib cage between its inner lining and the outer lining of the lungs. Occasionally, this cavity cannot resorb the CSF rapidly and the lung becomes compressed by the excess CSF resulting in difficulty in breathing. The catheter must be moved to a different cavity is such cases. Rarely, the catheter can rest on the diaphragm (the muscle at the base of the lungs used for breathing), causing irritation and hiccups.

While shunts were a major medical breakthrough, there are problems that still remain unsolved in the treatment of hydrocephalus, including shunt obstruction, infection, and overdrainage. Shunted NPH only has a success rate of about 50%. These same problems also exist with other conditions which are treated by CSF diversion, such as pseudotumor cerebri.

Accordingly, there remains a need for improved methods and devices for draining CSF to treat hydrocephalous, pseudotumor cerebri (IIH), or any other condition in which it is necessary to drain and/or cleanse CSF, potentially including Alzheimer's Disease.

SUMMARY OF THE INVENTION

Methods and devices are provided for shunting fluid, such as CSF. In one embodiment, a shunt device is provided and includes a housing having a fluid inlet port and a fluid outlet port. The fluid inlet and outlet ports are spaced a distance apart such that the fluid inlet port can be positioned to receive fluid from a source of cerebrospinal fluid, such as a subarachnoid space of a spinal column, and the fluid outlet port can be positioned to deliver fluid to a body cavity capable of accommodating cerebrospinal fluid drainage, such as an epidural space of a spinal column. The housing can also include a flow control component disposed therein and in fluid communication with the fluid inlet and outlet ports for controlling fluid flow from the fluid inlet port to the fluid outlet port.

The housing can have a variety of configurations, but in one embodiment the housing can include an elongate member extending therefrom and adapted to be disposed within a bone hole. The elongate member can have a variety of configurations, and it can include a first lumen in fluid communication with the fluid inlet port, and optionally a second lumen in fluid communication with the fluid outlet port. The elongate member can include other features, such as an external surface that is adapted to facilitate bone in-growth into the elongate member. For example, the elongate member can include bone-engaging surface features or a surface coating. In other embodiments, the device can also include a sleeve that is removably disposed around the elongate member and that is adapted to be disposed within a bone hole to anchor the elongate member within the bone hole. The sleeve can include a flange formed on a terminal end thereof and adapted to abut against a bone surface. The sleeve can also include a mating element formed on an inner surface thereof and adapted to removably mate to a complementary mating element formed on an outer surface of the elongate member.

In another embodiment, the housing can include a central portion that is adapted to be disposed within a lumen, and opposed first and second ends that are adapted to be positioned adjacent to opposed ends of the lumen to anchor the central portion within the lumen. The fluid inlet port can be formed in the first end of the housing and the fluid outlet port can be formed in the second end of the housing. The central portion can have a variety of configurations, but in one exemplary embodiment it can have a substantially cylindrical shape that is configured to be disposed within a substantially cylindrical lumen. The flow control component can be disposed within an inner lumen or bore formed in the central portion, or the bore can form the flow control component and it can have a diameter that is effective to control fluid flow therethrough. The first and second ends of the housing can also have a variety of configurations, but in one embodiment the first and second ends of the housing can be expandable.

In other aspects, a shunt system is provided having a shunt with first and second catheters and a flow control component coupled therebetween for controlling fluid flow from the first catheter to the second catheter. The system also includes a dual-lumen cannula having first and second lumens extending therethrough for respectively receiving the first and second catheters. The first lumen can have an opening that is positioned a distance apart from an opening in the second lumen such that the opening in the first lumen can be positioned to receive fluid from a subarachnoid space in a spinal column and the opening in the second lumen can be positioned to deliver fluid to an epidural space in a spinal column. In an exemplary embodiment, a portion of the first lumen adjacent to the opening is curved to guide the first catheter into the subarachnoid space, and a portion of the second lumen adjacent to the opening is curved to guide the second catheter into the epidural space.

Methods for shunting fluid are also provided, and in one embodiment the method can include positioning an inlet port of a shunt to receive fluid from a subarachnoid space in a spinal column, and positioning an outlet port of the shunt to deliver fluid to an epidural space of the spinal column such that fluid is drained from the subarachnoid space into the epidural space. While the shunt can have various configurations, one exemplary shunt includes a flow control component in fluid communication with the inlet and outlet ports for controlling fluid flow from the inlet port to the outlet port. The inlet port can be formed in a terminal end of a first catheter coupled to the flow control component, and the outlet port can be formed in a terminal end of a second catheter coupled to the flow control component. Positioning the inlet port can include forming a hole through a dura mater into the subarachnoid space and positioning at least a portion of the shunt through the hole in the dura mater to position the inlet port to receive fluid from the subarachnoid space, and positioning the outlet port can include forming a bone hole through a lamina into the epidural space and positioning at least a portion of the shunt through the bone hole in the lamina to position the outlet port to deliver fluid to the epidural space. In an exemplary embodiment, the shunt can include an elongate member and the inlet port can extend into a first lumen in the elongate member and the outlet port can extend into a second lumen in the elongate member. The elongate member can be inserted through the bone hole in the lamina. Inserting the elongate member can include threadably mating the elongate member to a sleeve positioned within the bone hole in the lamina. In other embodiments, positioning the inlet and outlet ports can include inserting a dual-lumen cannula through tissue to position an open end of a first lumen of the member within the epidural space, and to position an open end of a second lumen of the member within the subarachnoid space, and inserting a first catheter through the first lumen to position an end of the first catheter within the epidural space, and inserting a second catheter through the second lumen to position an end of the second catheter within the subarachnoid space.

The method can further include anchoring the flow control component adjacent to the spinal column. For example, the flow control component can be anchored to a vertebra. Exemplary anchoring locations include the spinous process of a vertebra. In other embodiments, the flow control component can be anchored to soft tissues surrounding a vertebra.

In yet another embodiment, a method of shunting fluid is provided and includes positioning an inlet port of a shunt at a location within a patient's body in which cerebrospinal fluid can flow into the inlet port, and anchoring a flow control component of the shunt to at least one of a vertebra and soft tissue surrounding a vertebra. The flow control component is disposed between the inlet port and an outlet port of the shunt for controlling cerebrospinal fluid flow from the inlet port to the outlet port. The method further includes positioning the outlet port of the shunt at a location within the patient's body in which cerebrospinal fluid flowing from the outlet port can be drained. In certain exemplary embodiments, the flow control component can be anchored to a location on a vertebra, such as of a spinous process, a lamina, and a transverse process.

BRIEF DESCRIPTION OF THE DRAWINGS

FIG. 11A is a top view illustration of a vertebra showing a sleeve implanted in the lamina.

FIG. 11B is a top view illustration of the vertebra of FIG. 11A, showing an elongate member about to be disposed through the outer sleeve of FIG. 11A to shunt fluid from the subarachnoid space to the epidural space.

FIG. 11C is a top view illustration of the vertebra of FIG. 11B, showing the elongate member through the outer sleeve.

DESCRIPTION OF THE PREFERRED EMBODIMENT

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Figures 1A, 1B:
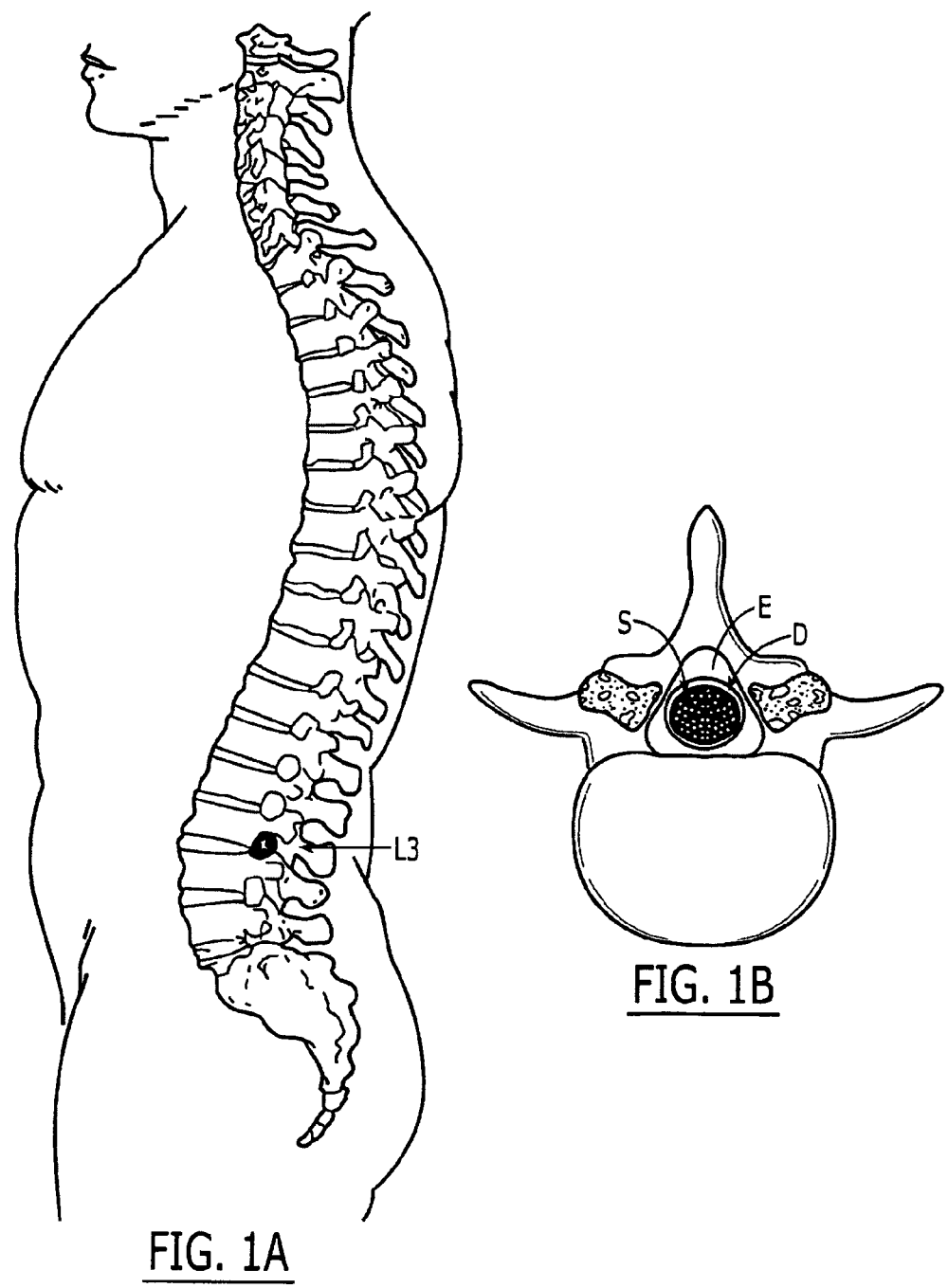
FIG. 1A is a side view of a mid-portion of a human body taken along the sagittal plane.
FIG. 1B is a top view of a human vertebral body taken along the axial plane.

The present invention provides methods and devices for shunting fluid to treat hydrocephalous, and in particular NPH, or Alzheimer's, Idiopathic Intracranial Hypertension (IIH), or any other condition in which it is necessary to drain and/or cleanse CSF. In general, the methods utilize a shunt that includes an inlet port, an outlet port, and a flow control component for controlling fluid flow from the inlet port to the outlet port. Exemplary shunts will be discussed in more detail below. The shunt can be implanted at a location along or within a patient's spinal column. FIGS. 1A and 1B illustrate sagittal and axial views of a human spinal column. As shown in FIG. 1A, in an exemplary embodiment a shunt is implanted in the lumbar spine, and more preferably at a mid location, such as the L3, in the lumbar spine. This is desirable to avoid unintentional contact with the spinal cord. The shunt can, however, be implanted at any level of the spine. The subarachnoid space S is shown in FIG. 1B and extends through the spinal canal along the length of the spinal column. The inlet port of a shunt can be implanted adjacent to or within this space, and the outlet port of a shunt can be implanted at a drainage site. While the drainage site can be any body cavity, it is preferably a location at which CSF can be reabsorbed, either directly or indirectly, into the blood stream. For example, CSF can be drained to the peritoneal cavity. In certain exemplary embodiments the fluid is drained into the epidural space E. As shown in FIG. 1B, the epidural space E surrounds the dura mater D, which in turn surrounds the subarachnoid space S. The particular implant location of the flow control component of the shunt can also vary. In one embodiment, the flow control component can be anchored to a vertebra or to soft tissue surrounding the vertebra. In other embodiments, the flow control component can be implanted within the epidural space E or within the dura mater D between the epidural and subarachnoid spaces E, S for shunting fluid from the subarachnoid space S into the epidural space E, as will be discussed below.

Figure 2:
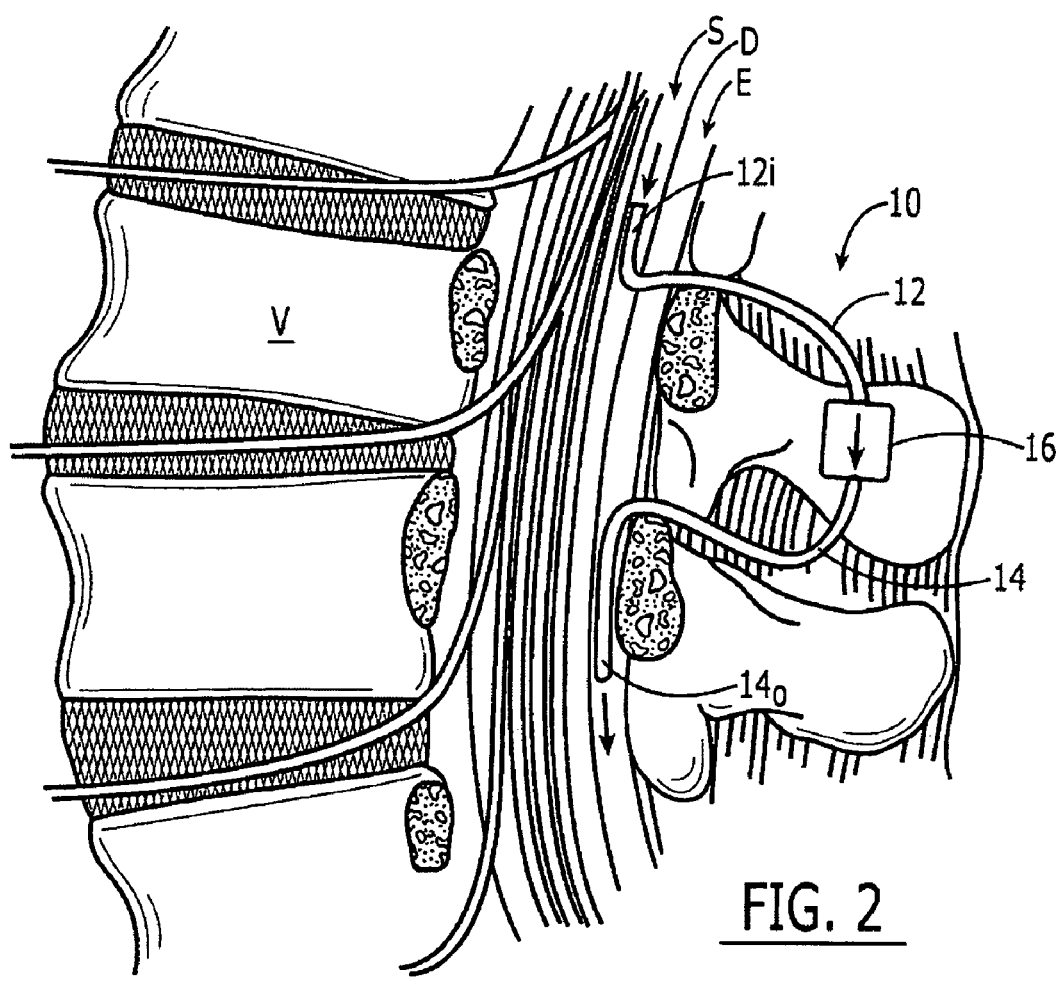
FIG. 2 is a side view of a portion of a spinal column showing one method for shunting fluid from a subarachnoid space into an epidural space.

FIG. 2 illustrates one exemplary embodiment of a shunt 10 for draining fluid from the subarachnoid space S to the epidural space E. The shunt 10 generally includes a first catheter 12 having a terminal end with one or more fluid inlet ports 12$i$ formed therein, and a second catheter 14 having a terminal end with one or more fluid outlet ports 14$o$ formed therein. A flow control component 16 is coupled between the first and second catheters 12, 14 and it is effective to control fluid flow from the first catheter 12 to the second catheter 14, thereby controlling CSF pressure. Virtually any flow control component configuration known in the art can be used, including flow regulating valve pins, differential pressure valves, slit valves, diaphragm valves, ball in cone valves, pin in seat valves, adjustable valves, electronically controlled valves, electronically controlled pump, etc.

Figure 3A:
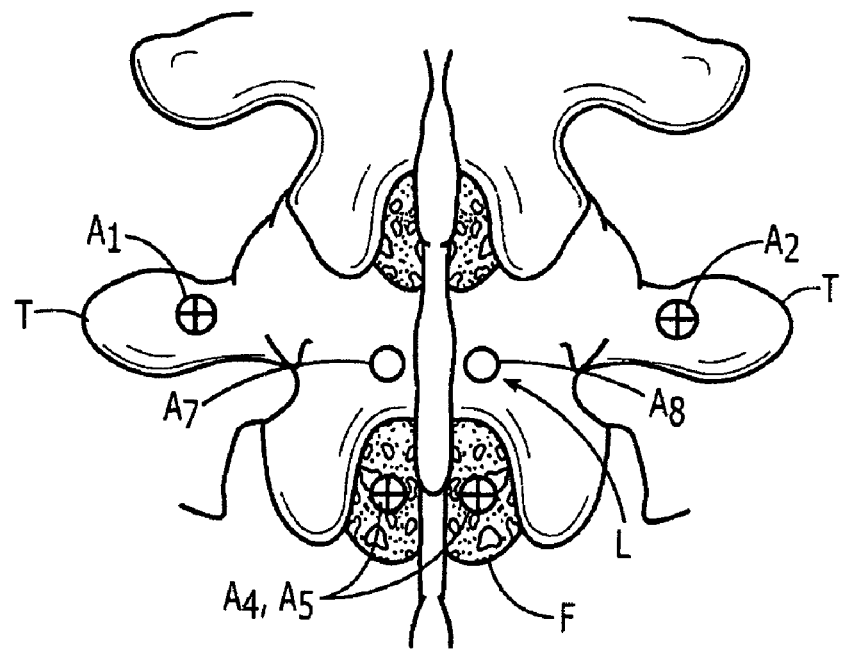
FIG. 3A is a posterior view of adjacent vertebral bodies showing various anchor locations for anchoring a shunt.
Figure 3B:
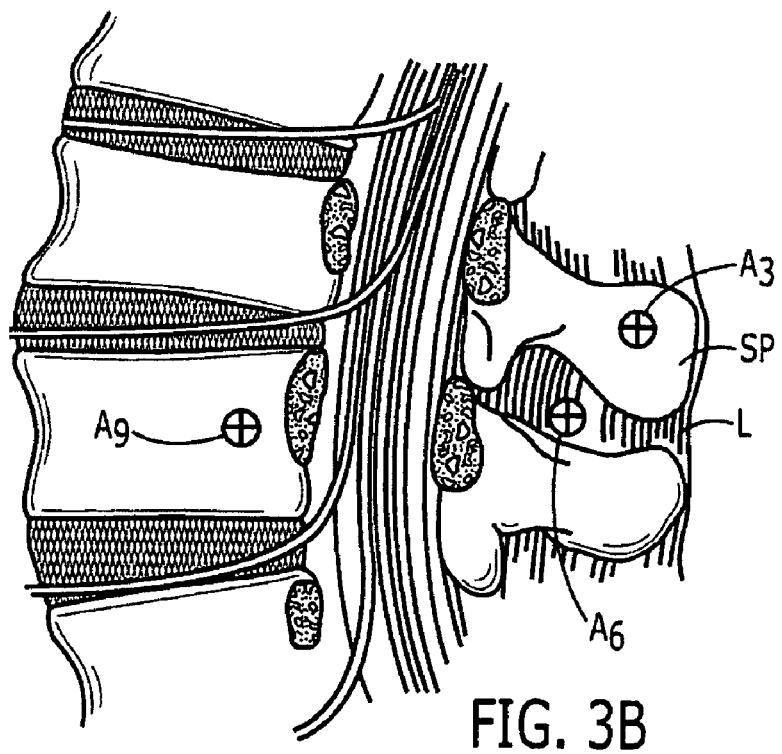
FIG. 3B is a side view of a portion of a spinal column showing various anchor locations for anchoring a shunt.

As further shown in FIG. 2, the flow control component 16 can be anchored to a vertebra V. The anchor site can be any location on the vertebra V, however exemplary anchor sites are shown in FIGS. 3A and 3B. FIG. 3A illustrates exemplary anchor sites A1, A2 on the transverse processes T, and FIG. 3B illustrates an anchor site A3 on the spinous process SP of the vertebrae V, and anchor site A9 in the vertebral body. In other embodiments, the flow control component 16 can be disposed within or anchored to soft tissue surrounding the vertebrae, such as at anchor sites A4, A5 in the ligamentum flavum F, shown in FIG. 3A, or at anchor site A6 in the interspinous ligaments L, shown in FIG. 3B. While the soft tissue or bone may be effective to retain the flow control component 16 in place, various techniques can be used to anchor the flow control component 16 to a vertebra V or to soft tissue X surrounding a vertebra, including bone screws, sutures, adhesives, etc.

Figure 4:
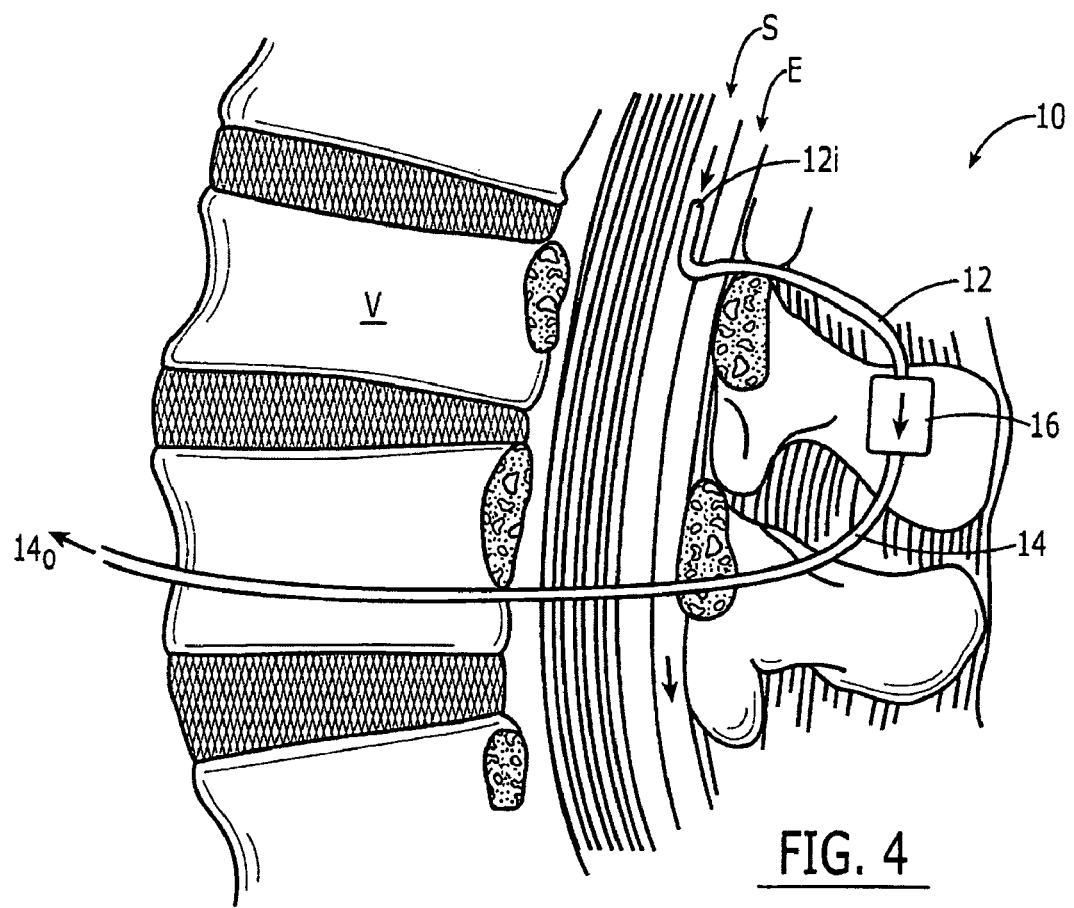
FIG. 4 is a side view of a portion of a spinal column showing another method for shunting fluid from a subarachnoid space into a drainage site in the body.

While FIG. 2 illustrates the second catheter 14 draining fluid to the epidural space E, other drainage sites within the body can be used. FIG. 4 illustrates the shunt 10 of FIG. 2 with the second catheter 14 extending out of the spinal column to drain fluid into the peritoneum, or other drainage sites such as the atrium or chest cavity. The second catheter 14 can extend around the spinal column to allow the outlet port 14$o$ on the second catheter 14 to be implanted at other locations within the body.

Figure 5:
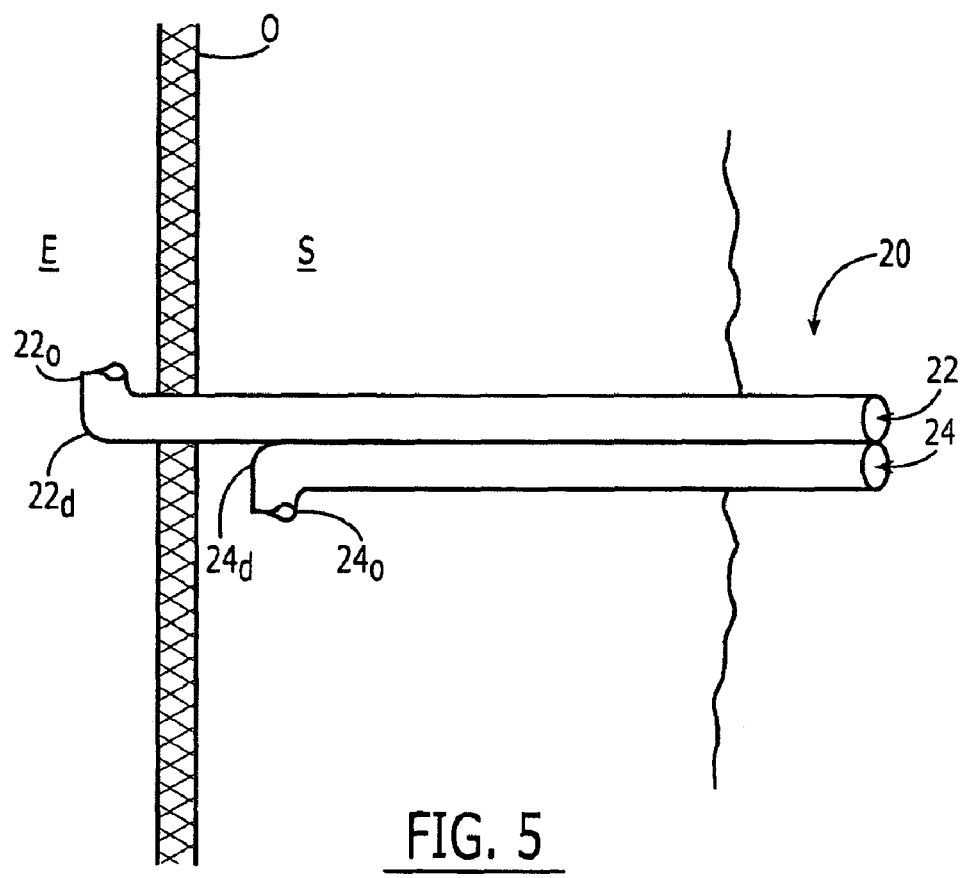
FIG. 5 is a side view of one embodiment of an insertion tool for inserting first and second catheters into the subarachnoid and epidural spaces, respectively.

The shunt can also be implanted using a variety of techniques. In one exemplary embodiment, shown in FIG. 2, the first catheter 12 extends from the flow control component 16 through the ligamentum flavum between adjacent vertebra and into or at least adjacent to the subarachnoid space S, and the second catheter 14 extends from the flow control component 16 through the ligamentum flavum between adjacent vertebra and into or at least adjacent to the epidural space E. While the catheters 12, 14 can merely be guided through the ligaments using guide wires or other known techniques, FIG. 5 illustrates one exemplary embodiment of a tool 20 for introducing the first and second catheters 12, 14 into or adjacent to the epidural and subarachnoid spaces E, S. As shown, the tool 20 is in the form of a hollow elongate cannula having two lumens 22, 24 extending therethrough. The first lumen 22 has an outlet 22o that is positioned proximal to an outlet 24o of the second lumen 24. As a result, when the dual-lumen cannula 20 is inserted through the ligament, the outlet 22o in the first lumen 22 can be positioned adjacent to or within the epidural space E, while the outlet 24o in the second lumen 24 can be positioned adjacent to or within the subarachnoid space S. A person skilled in the art will appreciate that the distance between the outlet 22o, 24o of each lumen 22, 24 can be adapted to obtain the desired result in use of the device. As further shown in FIG. 5, a distal portion 22d, 24d of each lumen 22, 24 adjacent to the outlet 22o, 24o can include features to help guide the catheters into or adjacent to the epidural and subarachnoid spaces E, S. In an exemplary embodiment, the portion 22d, 24d of each lumen adjacent the outlet 22o, 24o is curved to turn a catheter inserted therethrough about 90.degree., thereby directing the catheter such that it will extend axially along the patient's spinal column.

In other embodiments, rather than anchoring a flow control component to the vertebra or soft tissues and extending catheters into or adjacent to the epidural and subarachnoid spaces E, S, the shunt can be configured to be anchored directly to the lamina, or to be implanted in the epidural space E or in the dura mater D between the epidural and subarachnoid spaces E, S. FIGS. 6-11 illustrate various exemplary embodiments and techniques for implanting a shunt in the lamina, epidural space E, or dura mater D.

Figure 6:
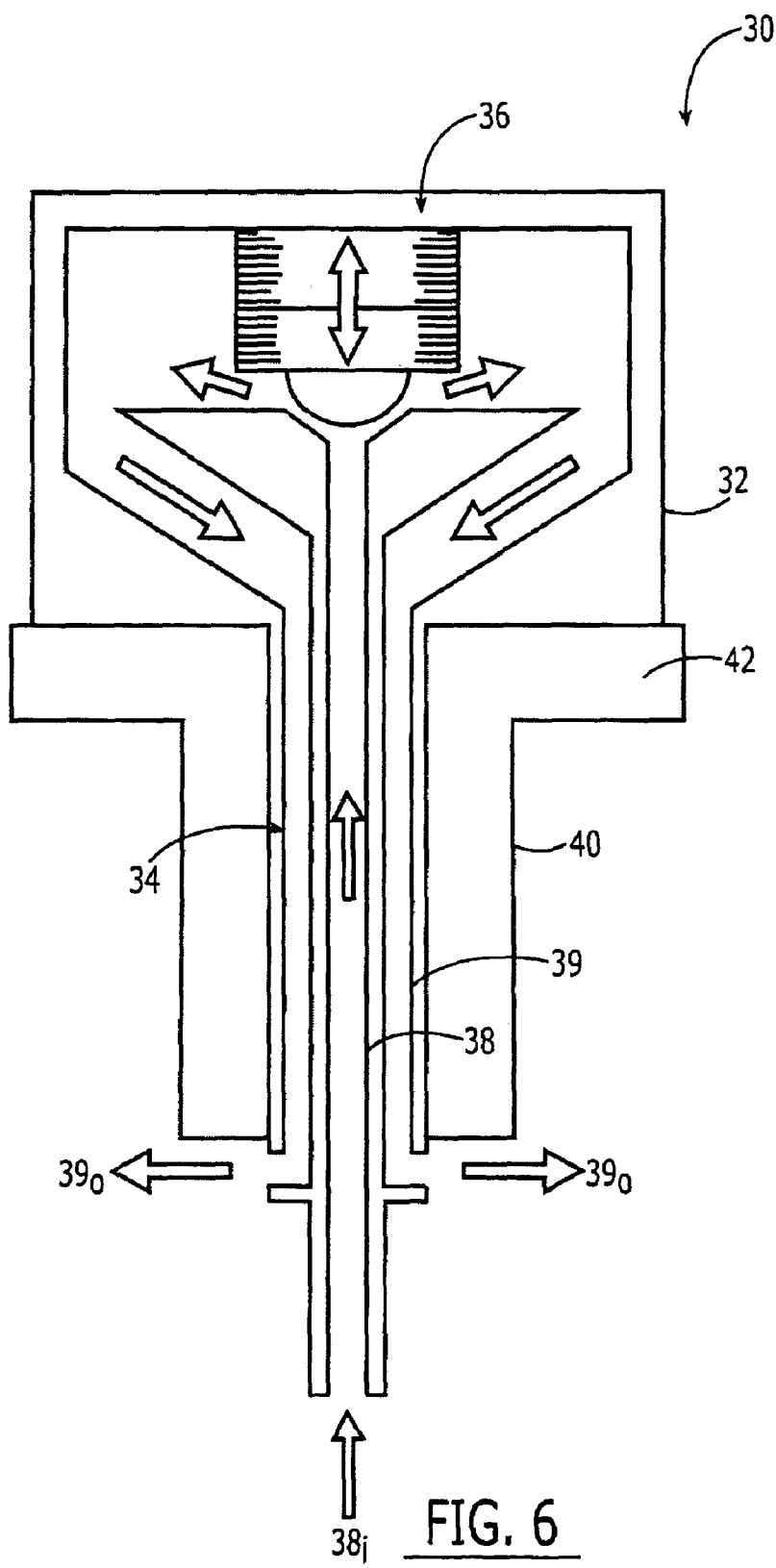
FIG. 6 is a side view of one exemplary embodiment of a shunt for shunting fluid from a subarachnoid space into an epidural space.

In the embodiment shown in FIG. 6, the shunt 30 generally includes a housing 32 having an elongate member 34 extending therefrom and configured to be disposed through bone. The housing 32 can have a variety of shapes and sizes, but it is preferably adapted to retain a flow control component 36 therein, as will be discussed below. In the illustrated embodiment, the housing 32 has a generally hollow cylindrical shape, and the elongate member 34 extends from a distal end of the housing 32. The elongate member 34 can have a variety of configurations, shapes, and sizes, and it can be rigid, semi-rigid, or flexible. For example, the elongate member 34 can be in the form of a rigid needle or cannula, or a flexible tubular member, such as a catheter. In the embodiment shown in FIG. 6 the elongate member 34 is in the form of a cannula that is adapted to be disposed within a bone hole. The elongate member 34 can be integrally formed with the housing 32, or it can be removably attached to the housing 32. For example, a hub or other attachment mechanism can be formed on a proximal end of the elongate member 34 for removably attaching the elongate member 34 to the housing 32. The elongate member 34 can also include a first lumen 38 formed therein and having a fluid inlet port 38i, and a second lumen 39 formed therein and having a fluid outlet port 39o. The fluid inlet and outlet ports 38i, 39o can be spaced a distance apart from one another along an axis of the elongate member to allow the fluid inlet port 38i to be positioned adjacent to or within the subarachnoid space S, while the fluid outlet port 39o is positioned adjacent to or within the epidural space E, as will be explained in more detail below. While various techniques can be used to position the inlet and outlet ports 38i, 39o a distance apart from one another, in the embodiment shown in FIG. 6 the first lumen 38 extends a distance beyond the second lumen 39. As a result, the outlet port 39o in the second lumen 39 is proximal of the inlet port 38i in the first lumen 38. As further shown, the first lumen 38 extends through the second lumen 39 such that the lumens 38, 39 are coaxial. The lumens 38, 39 can, however, be positioned side-by-side or they can have various other configurations.

Figure 7:
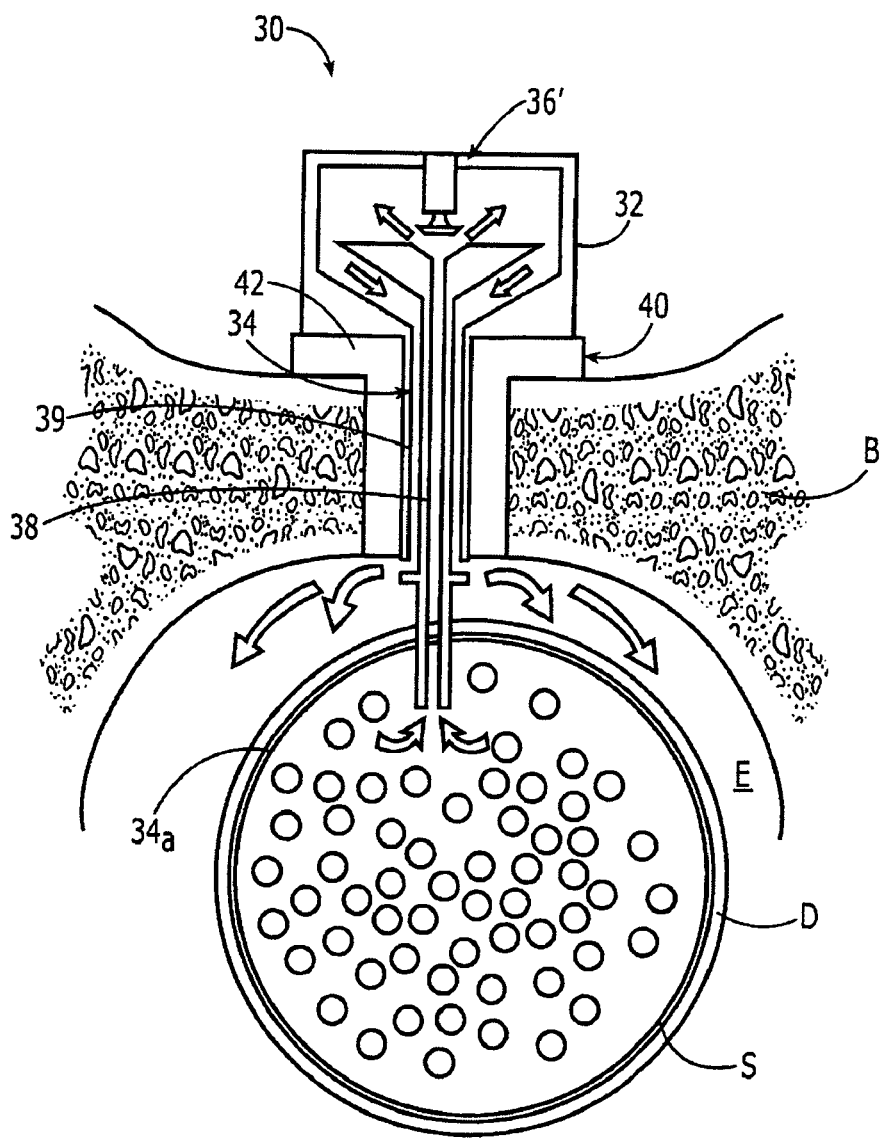
FIG. 7 is a top view of another the shunt of FIG. 6 having another embodiment of a flow control component disposed therein, and being implanted in a lamina of a vertebra to shunt fluid from a subarachnoid space into an epidural space.
Figure 8:
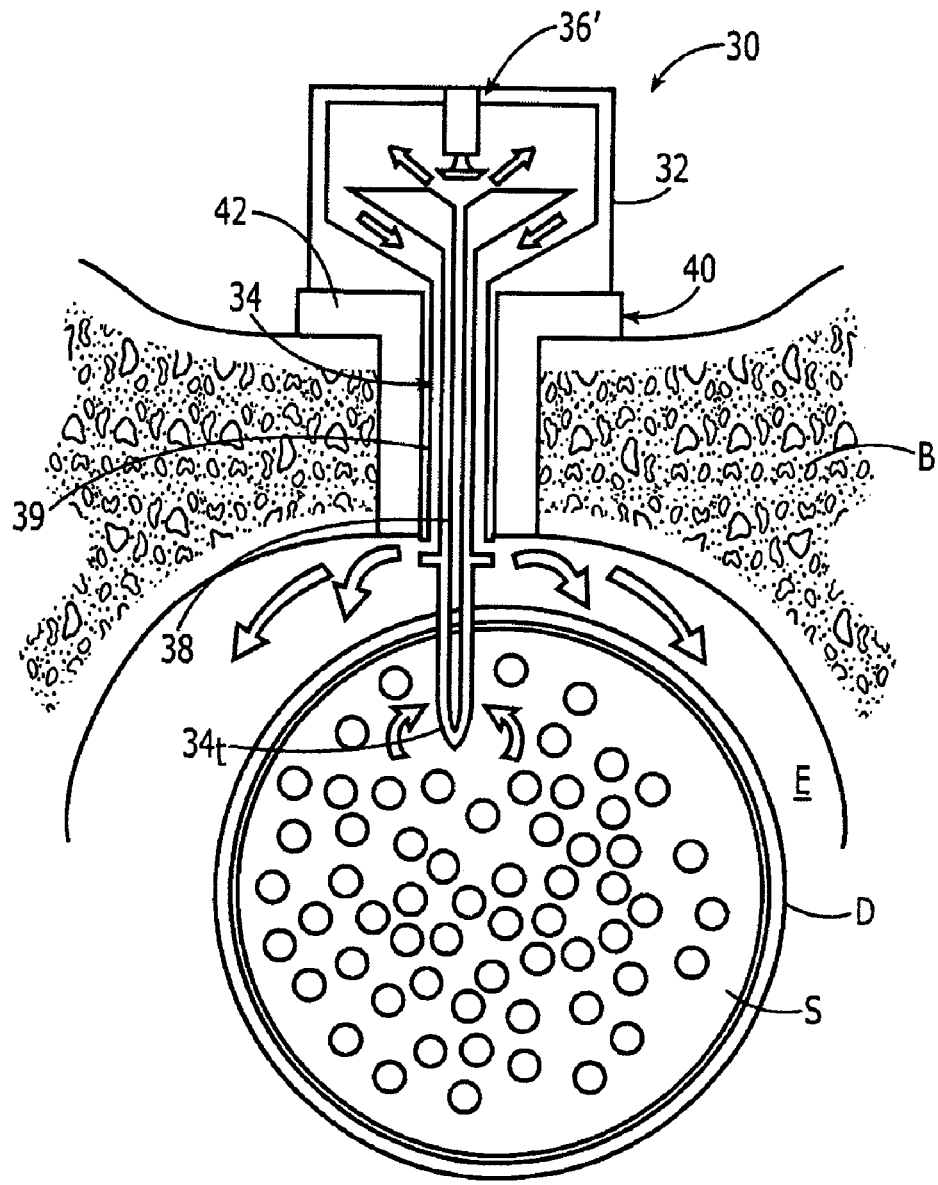
FIG. 8 is a top view of the shunt of FIG. 6 having a distal, tissue-piercing tip, and being implanted in a lamina of a vertebra to shunt fluid from a subarachnoid space into an epidural space.

In order to allow fluid to flow through the shunt 30, the lumens 38, 39 can be in fluid communication with a flow control component 36 disposed therebetween. As shown in FIG. 6, a flow control component 36 is disposed within the proximal portion of the housing 32 and is positioned to control fluid flow from the first lumen 38 into the second lumen 39. In particular, the first lumen 38 extends through the elongate member 34 directly to the flow control component 36 in the housing 32. The fluid can then flow through the flow control component 36 and directly into the second lumen 39. The flow control component 36 can have virtually any configuration known in the art. In the illustrated embodiment, a bellows valve is used to control fluid flow therethrough. FIGS. 7 and 8 illustrate the shunt of FIG. 6 having another embodiment of a flow control component 36' in the form of a flow regulating pin for regulating fluid flow through the flow control component 36'. Other exemplary flow control component types include, by way of non-limiting example, differential pressure valves, slit valves, diaphragm valves, ball in cone valves, pin in seat valves, adjustable valves, electronically controlled valves, electronically controlled pumps, etc.

In use, referring to FIGS. 7 and 8, the shunt 30 is adapted to be implanted such that the inlet port 38i is disposed adjacent to or within the subarachnoid space S and the outlet port 39o is disposed adjacent to or within the epidural space E, thereby allowing CSF to flow into the first lumen 38, through the flow control component 36', into the second lumen 39, and out of the outlet port 39o into the epidural space E. While the shunt 30 can be implanted at various locations to position the inlet and outlet ports 38i, 39o at the desired location, in an exemplary embodiment the shunt 30 is implanted in the lamina B. FIG. 3A illustrates two anchor sites A7, A8 in the lamina B. Referring back to FIGS. 7 and 8, a bone hole can be formed in the lamina B and the elongate member 34 can be inserted therethrough. Various techniques can be used to anchor the shunt 30 to the lamina B. For example, the outer surface of the elongate member 34 can include threads or other surface features formed thereon and configured to engage the bone surrounding the bone hole. The elongate member can also or alternatively include a surface coating, such as a porous coating or hydroxyapatite. Alternatively, as shown in FIGS. 6-8, an elongate body or sleeve, such as a cannulated bolt 40, can be implanted in the lamina B for anchoring the shunt 30. The cannulated bolt 40 is sized to be disposed within a bone hole, and it can include a flange 42 formed on one end thereof and adapted to abut against the bone surface adjacent the bone hole to prevent the cannulated bolt 40 from passing through the bone hole. The cannulated bolt 40 can also include threads formed thereon for threading the bolt 40 into the bone hole, or it can be attached to the lamina B using other techniques known in the art. In an exemplary embodiment, the cannulated bolt 40 is threaded and a bolt applier is used to thread the bolt 40 into a bone hole formed in the lamina B. The elongate member 34 can be inserted through the cannulated bolt 40 to position the inlet and outlet ports 38i, 39o in or adjacent to the subarachnoid and epidural spaces S, E, respectively. In one exemplary embodiment, the elongate member 32 can include a mating element, such as threads, formed thereon for mating to a complementary mating element formed in the inner lumen of the cannulated bolt 40. Such a configuration allows the shunt 30 to be removed and/or replaced, if necessary.

In order to position the inlet and outlet ports 38*i*, 39*o* in or adjacent to the subarachnoid and epidural spaces S, E, the elongate member 34 needs to extend through the dura mater D which is located between the subarachnoid and epidural spaces S, E. In one embodiment, shown in FIG. 7, the distal-most end of the elongate member 34 can include a blunt tip 34*a*. Various techniques and devices known in the art can be used to form a puncture hole in the dura mater D and/or to guide the blunt tip 34*a* into the subarachnoid space S. Alternatively, the distal-most end of the elongate member 34 can include a tissue-penetrating tip 34*t*, such as a sharp pointed or spiked tip, formed thereon as shown in FIG. 8. The tip 34*t* can be used to penetrate through the dura mater D as the shunt 30 is being implanted.

Once the shunt 30 is implanted, as shown in FIGS. 7 and 8, CSF fluid flowing through the subarachnoid space S will flow into the inlet port 38*i* of the first lumen 38, and out of the outlet port 39*o* in the second lumen 39 to be delivered directly into the epidural space E, whereby at least some of the CSF can be reabsorbed back into the blood stream. The flow control component 36, 36' will regulate fluid flow through the shunt 30, thereby controlling CSF pressure.

Figure 9:
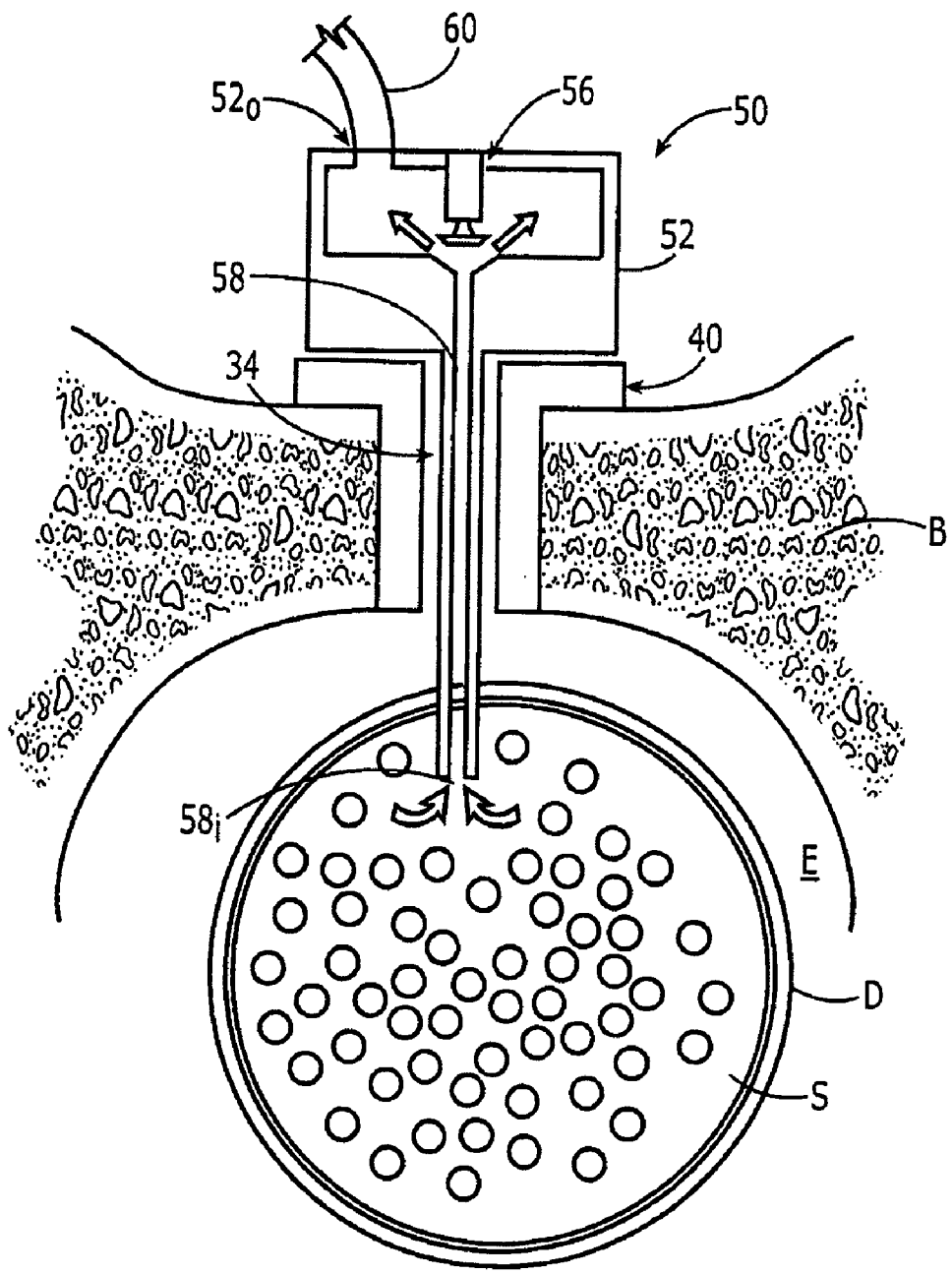
FIG. 9 is a top view of yet another embodiment of a shunt for shunting fluid from a subarachnoid space into another drainage site located in the body, showing the shunt implanted in a lamina of a vertebra.

FIG. 9 illustrates another embodiment a shunt 50 for treating CSF. In this embodiment, the shunt 50 is adapted to be implanted in the lamina B to drain CSF from the subarachnoid space S to other locations within the body. In particular, the shunt 50 includes a housing 52 having an elongate member 54 extending therefrom and adapted to extend into the subarachnoid space S. The housing 52 is similar to the housing 32 described with respect to FIG. 6, and contains a flow control component 56 disposed therein for controlling fluid flow therethrough. The elongate member 54, on the other hand, only includes one lumen 58 extending therethrough.

The lumen 58 includes an inlet port 58*i* at a distal-most end thereof, and fluid flowing through the lumen 58 is delivered to the flow control component 56. Rather than having a return lumen for delivering fluid to the epidural space E, an outlet port 52*o* can be formed in the housing 52 and a catheter 60 can be coupled thereto. The catheter 60 can deliver fluid from the outlet port 52*o* to another drainage site within the body, such as the peritoneal cavity. A person skilled in the art will appreciate that the housing 52 and elongate member 54 can have a variety of other shapes and sizes, and they can be integrally formed with one another or removably matable to one another.

In use, as with the embodiment shown in FIGS. 7 and 8, the shunt 50 of FIG. 9 can be implanted in the lamina B by inserting the elongate member 54 through a bone hole formed in the lamina B. The elongate member 54 can mate directly to the lamina B, or it can mate to a sleeve, such as a cannulated bolt 40 as previously described, disposed within the bone hole. The distal end of the elongate member 54 is configured to extend through the dura mater D, and thus it can be inserted through a pre-formed puncture hole formed in the dura mater D using various techniques known in the art, or it can include a tissue-penetrating tip formed thereon for puncturing through the dura mater D. The catheter 60 extending from the outlet port 52*o* can extend around or between the adjacent vertebrae to be positioned at another drainage site in the body.

Figure 10C:
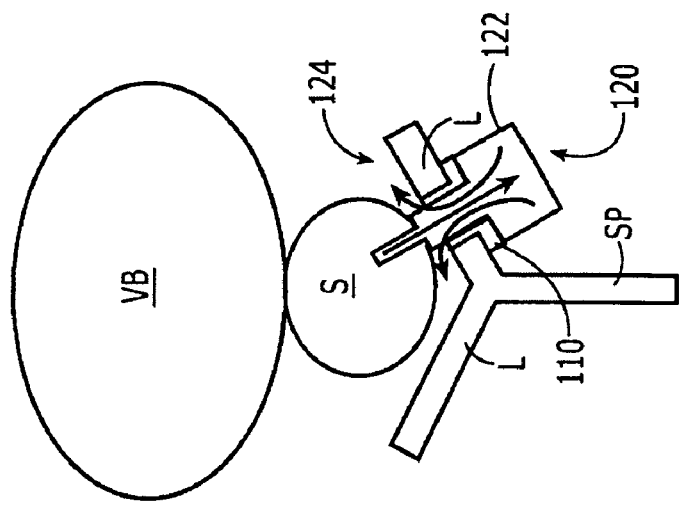
FIG. 10C is a top view illustration of the vertebra of FIG. 10B, showing the shunt disposed through the outer sleeve for shunting fluid from the subarachnoid space to the epidural space.
Figure 10B:
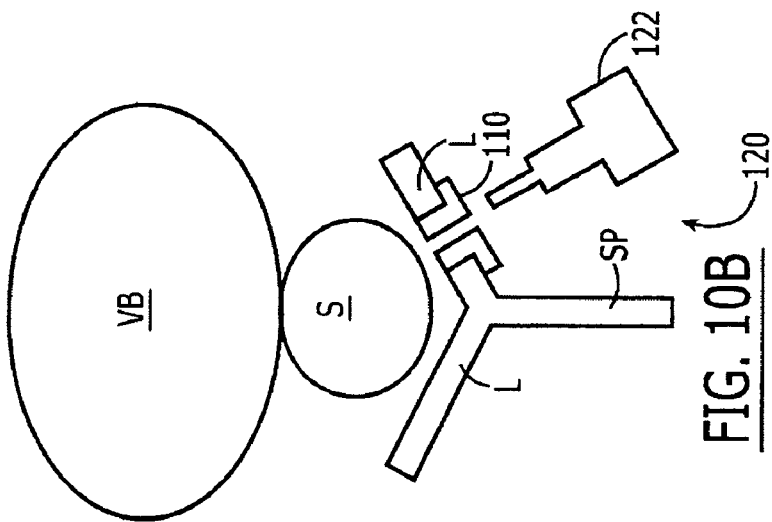
FIG. 10B is a top view illustration of the vertebra of FIG. 10A, showing a shunt about to be disposed through the outer sleeve of FIG. 10A to shunt fluid from the subarachnoid space to the epidural space.

A person skilled in the art will appreciate that particular method of implanting the shunt will vary depending on the particular configuration of the shunt, and whether it includes one, two, or three pieces. For example, referring to the shunt 30 of FIG. 6, the housing 32 and elongate member 34 can form a single piece that can be directly implanted in the lamina to shunt fluid. Alternatively, the shunt 30 can have a two-piece configuration where the housing 32 and elongate member 34 form a first piece and the sleeve, e.g., the cannulated bolt 40, forms the second piece, or where the housing 32 forms the first piece and the elongate member 34 forms the second piece. In another embodiment, the shunt 30 can have a three piece configuration that includes the housing 32, a separate elongate member 34, and a separate sleeve, e.g., the cannulated bolt 40. Accordingly, the method of implanting the shunt will vary depending on the configuration of the shunt. By way of non-limiting example, FIGS. 10A-10C illustrates one exemplary method for implanting a two-piece shunt, and FIGS. 11A-11E illustrate one exemplary method for implanting a three-piece shunt.

Figure 10A:
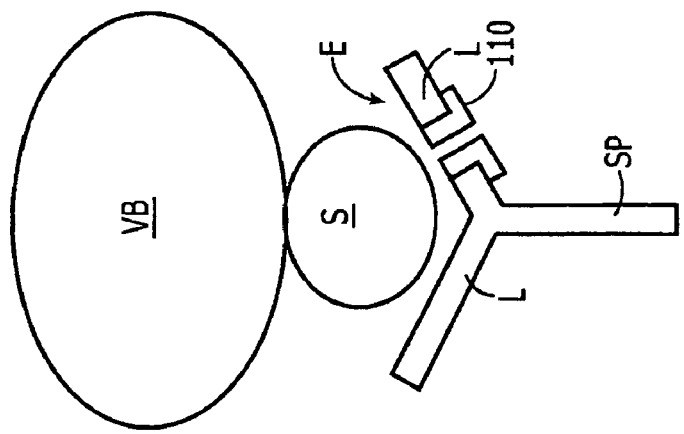
FIG. 10A is a top view illustration of a vertebra showing a sleeve implanted in the lamina.

FIG. 10A illustrates a vertebra, which includes the vertebral body VB, the spinous process SP, the lamina L, and the subarachnoid space S. The epidural space E is the area surrounding the subarachnoid space S. As shown in FIG. 10A, a bore can be formed in the lamina and a sleeve 110 can be implanted in the bore to form a pathway through the lamina. A shunt 120 having a shunt housing 122 containing a flow control component (not shown) and an elongate member 124 extending from the shunt housing 122 can be inserted into and mated with the sleeve 110, as shown in FIGS. 10B and 10C. The elongate member 124 will extend into the subarachnoid space S, allowing CSF to flow into the elongate member 124 and into the shunt housing 122. The flow control component in the shunt housing 122 will redirect the CSF to one or more outlets ports formed in the shunt and positioned within the epidural space E, thereby draining CSF from the subarachnoid space S to the epidural space E.

Figure 11E:
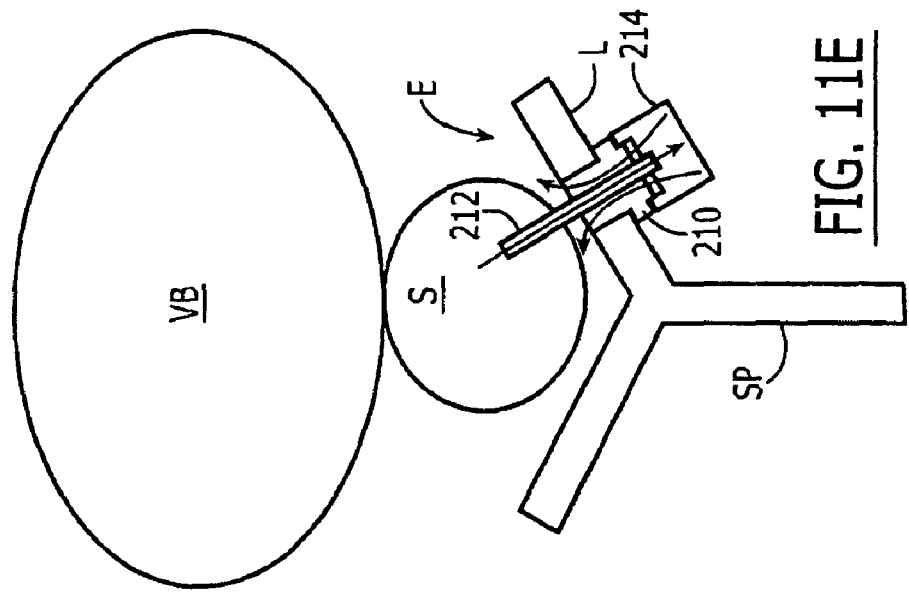
FIG. 11E is a top view illustration of the vertebra of FIG. 11D, showing the shunt housing coupled to the elongate member and the outer sleeve for shunting fluid from the subarachnoid space to the epidural space.
Figure 11D:
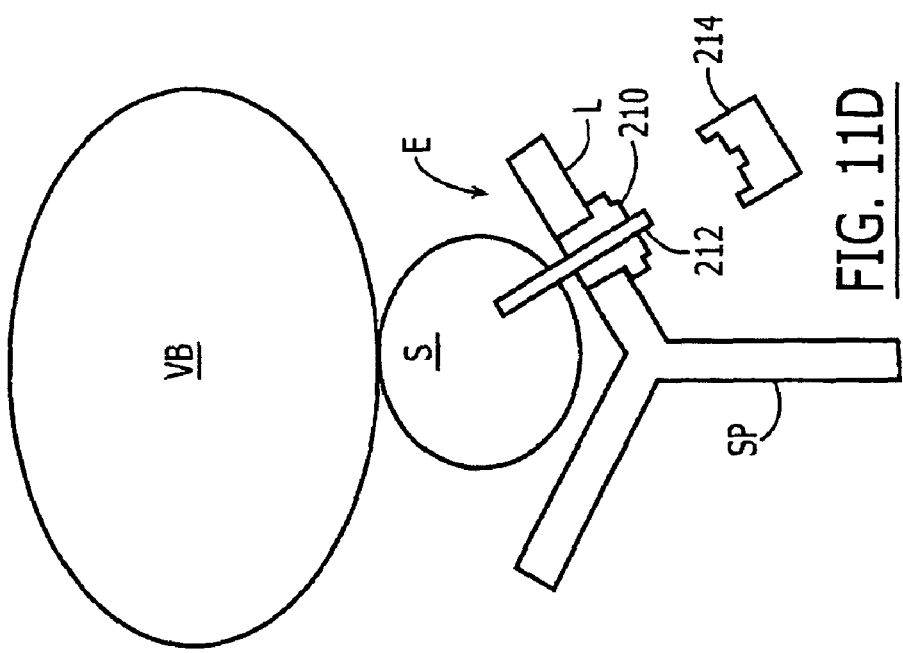
FIG. 11D is a top view illustration of the vertebra of FIG. 11C, showing the a shunt housing about to be coupled to the elongate member and sleeve.

FIG. 11A similarly illustrates a vertebra, which includes the vertebral body VB, the spinous process SP, the lamina L, and the subarachnoid space S. The epidural space E is the area surrounding the subarachnoid space S. As shown, a bore can be formed in the lamina and a sleeve 210 can be implanted in the bore to form a pathway through the lamina. An elongate member 212, such as a cannula or catheter, can be inserted into the sleeve 210, as shown in FIGS. 11B and 11C. As a result, the elongate member 212 will have a first end extending outside of the sleeve 210, and a second end that extends into the subarachnoid space S, allowing CSF to flow into the elongate member 212. A third piece in the form of a shunt housing 214 having a flow control component therein can then be attached to the sleeve 210, as shown in FIGS. 11D and 11E, to receive CSF from the elongate member 212 and to redirect the CSF into the epidural space E, thereby draining CSF from the subarachnoid space S to the epidural space—E. The CSF can either flow through a second, outlet lumen formed in the elongate member 212, it can flow between the elongate member 212 and the sleeve 210, or it can flow through conduits in the sleeve. A person skilled in the art will appreciate that threads of other mating techniques can be used to mate the shunt housing 214 to the sleeve 210. The shunt housing 214 can also mate to or engage a proximal end of the elongate member 212 to retain the elongate member 212 therein.

Figure 12:
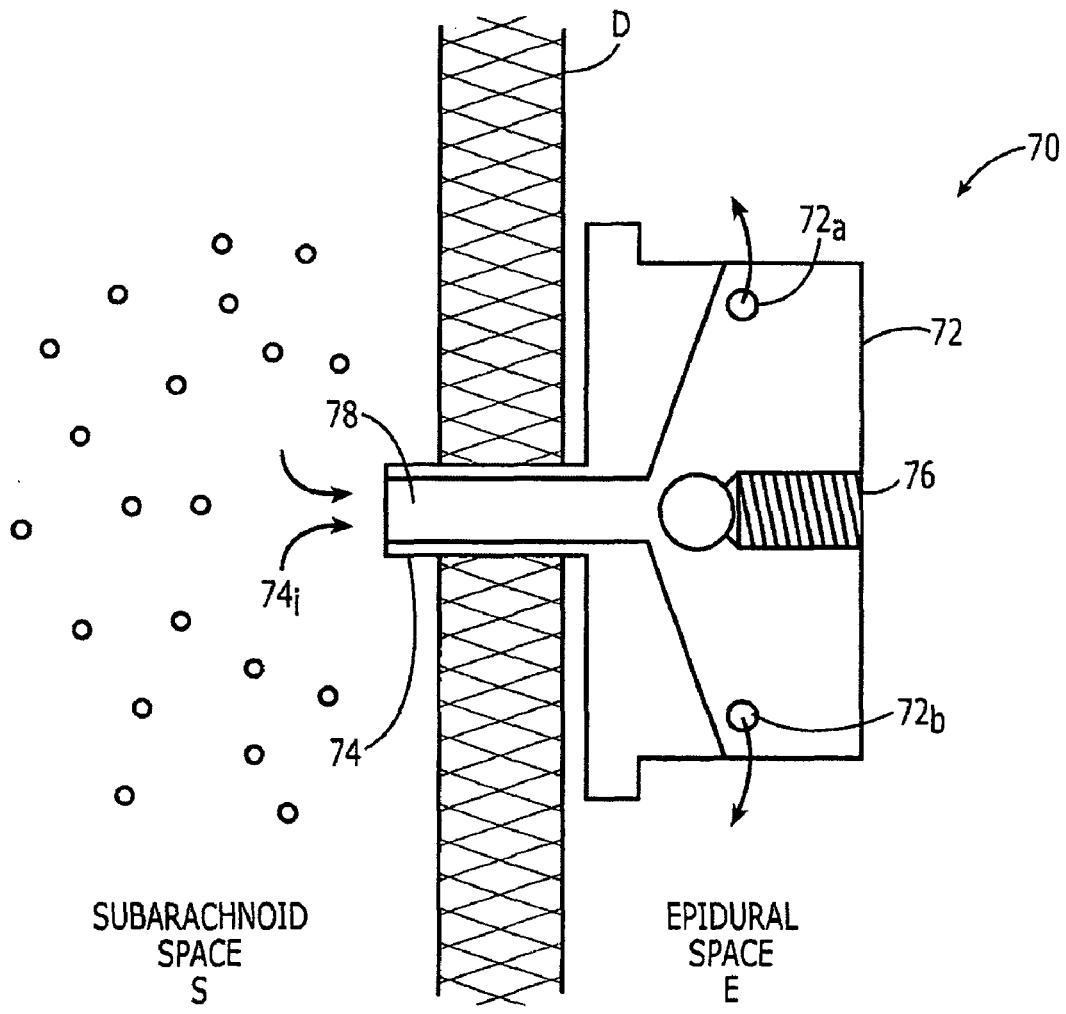
FIG. 12 is a side view of a shunt implanted in the epidural space for shunting fluid from the subarachnoid space into the epidural space in accordance with another exemplary embodiment.

As indicated above, in other embodiments a shunt can be implanted within the dura mater D between the subarachnoid and epidural spaces S, E. FIG. 12 illustrates one embodiment of such a shunt 70. As shown, the shunt 70 is similar to the shunt 50 of FIG. 9, and includes a housing 72 having a flow control component 76 disposed therein, and an elongate member 74 extending from the housing 72 and having a lumen 78 in fluid communication with the flow control component 76. An inlet port 74*i* is formed in the distal end of the elongate member 74, and one or more outlet port 72*a*, 72*b* can be formed in the housing 72. In this embodiment, the elongate member 74 is shorter in length than the shunt 50 of FIG. 9 as it only needs to extend through the dura mater D, rather than through the lamina B, epidural space E, and the dura mater D, as with the FIG. 9 embodiment. The shunt 70 also does not include a catheter, as the outlet ports 72a, 72b can release fluid directly into the epidural space E.

In use, as shown, the shunt 70 is implanted within the epidural space E, and the elongate member 74 is positioned through the dura mater D such that the inlet port 74i is disposed adjacent to or within the subarachnoid space S. As previously explained, various devices known in the art can be used to penetrate through the dura mater D and/or guide the elongate member 74 therethrough, or the elongate member 74 can include a tissue-penetrating tip formed thereon. In order to anchor the shunt 70 within the epidural space E, the elongate member 74 can include surface features and/or coatings formed or disposed thereon to prevent removal thereof from the dura mater D, or the housing 72 can be attached to the dura mater D using sutures, bone screws, or other mating techniques. Once the shunt 70 is implanted, CSF can flow from the subarachnoid space S through the shunt 70, where it is released in a controlled manner into or adjacent to the epidural space E.

Figure 13A:
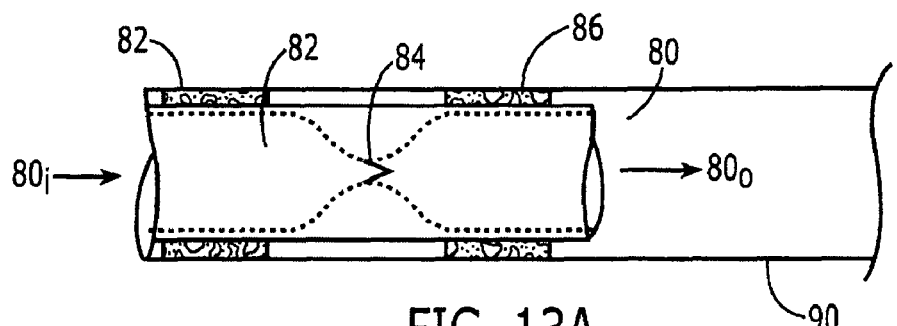
FIG. 13A is a side view of one exemplary embodiment of a shunt having a sleeve disposed therearound.
Figure 13B:
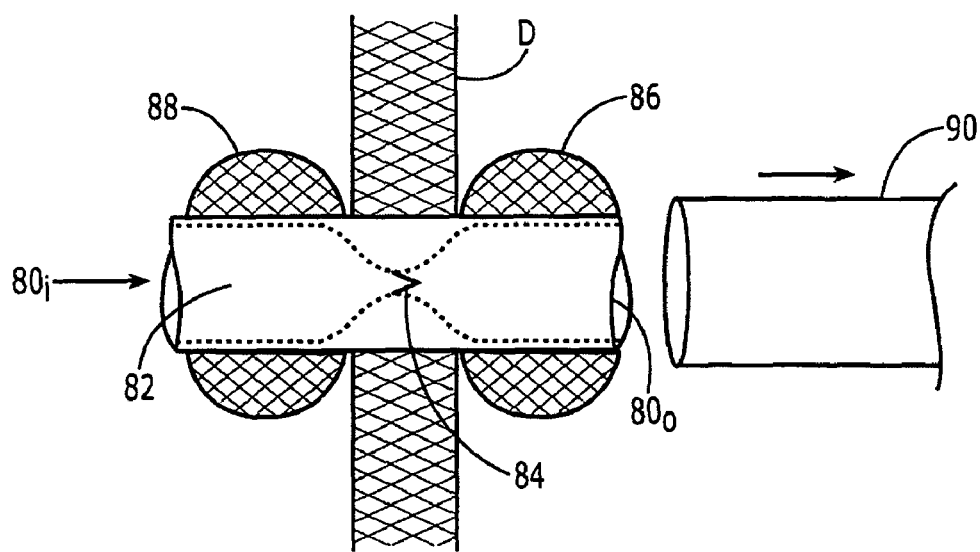
FIG. 13B is a side view of the shunt of FIG. 13A with the sleeve removing, showing anchor members expanded to anchor the shunt within a bone or tissue hole.

FIGS. 13A and 13B illustrate another embodiment of a shunt that can be implanted within the dura mater D. While the shunt can have a variety of configurations, as shown the shunt 80 is in the form of a tubular body having a lumen 82 extending therethrough between an inlet 80i and an outlet 80o. The lumen 82 functions as a conduit for fluid to flow from the subarachnoid space S into the epidural space E. The lumen 82 can include a flow control component disposed therein, or the lumen 82 can form the flow control component. For example, the lumen can have a diameter that is sized to regulate fluid flow therethrough. A one-way valve, such as a duck-bill valve 84, can be formed within the lumen 82 for preventing fluid from flow into the subarachnoid space S.

The shunt 80 can also include an anchor member formed on or coupled each end thereof for anchoring the shunt 80 within the dura mater D. The anchor members can have a variety of configurations, but in an exemplary embodiment the anchor members are expandable. For example, each anchor member can be in the form of an expandable balloon. In the embodiment shown in FIGS. 13A and 13B, the anchors members are expandable rings 86, 88 that are coupled to and disposed around the shunt 80, and that are formed from a shape memory material, such as Nitinol, such that the anchors 86, 88 are self-expanding. A sleeve, such as a cannula 90 shown in FIG. 13A, can be disposed around the shunt 80 to retain the anchor members 86, 88 in an initial, unexpanded configuration. Once the sleeve 90 is inserted into or through the dura mater D, the sleeve 90 can be retracted, or the shunt 80 can be pushed out of the sleeve 90, to allow the anchor members 86, 88 to expand, as shown in FIG. 13B. The shunt 80 is positioned such that one anchor member 88 is disposed adjacent to or within the subarachnoid space S and the other anchor member 86 is disposed adjacent to or within the epidural space E. As a result, the anchor members 86, 88 will engage the dura mater D therebetween, thereby anchoring the shunt 80 in the dura mater D. A person skilled in the art will appreciate that a variety of other anchoring techniques can be used, and that in other embodiments the shunt can be configured to be retained within the dura mater D without the use of anchor members. Sutures, adhesive, or other techniques can also or alternatively be used.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A shunt for transport of cerebrospinal fluid from a spinal subarachnoid space of a spine to an epidural space of the spine, the shunt comprising in combination:
   a cerebrospinal fluid inlet;
   a cerebrospinal fluid outlet;
   a walled fluid pathway between said cerebrospinal fluid inlet and said cerebrospinal fluid outlet;
   said walled fluid pathway coupling said cerebrospinal fluid inlet to said cerebrospinal fluid outlet with a spacing between said cerebrospinal fluid inlet and said cerebrospinal fluid outlet sufficient to allow said cerebrospinal fluid inlet to be placed within the subarachnoid space of the spine and for the cerebrospinal fluid outlet to be placed within the epidural space of the spine;
   a flow controller on said fluid pathway and adapted to control flow between said cerebrospinal fluid inlet and said cerebrospinal fluid outlet;
   an anchor coupled to said walled fluid pathway;
   said anchor adapted to be affixed to an anatomical structure proximate to the spine; and
   said cerebrospinal fluid inlet and said cerebrospinal fluid outlet located on a common side of said anchor.

2. The shunt of claim 1 wherein said walled fluid pathway includes at least one conduit completely containing fluid flow between said cerebrospinal fluid inlet and said cerebrospinal fluid outlet.

3. The shunt of claim 1 wherein said walled fluid pathway includes at least two parts with one of said parts adjacent said cerebrospinal fluid inlet and the other of said at least two parts adjacent said cerebrospinal fluid outlet.

4. The shunt of claim 1 wherein said cerebrospinal fluid outlet includes a plurality of separate outlet ports.

5. The shunt of claim 1 wherein said walled fluid pathway has a fixed distance between said cerebrospinal fluid inlet and said cerebrospinal fluid outlet.

6. The shunt of claim 1 wherein said walled fluid pathway includes an elongate portion passing through said anchor.

7. The shunt of claim 1 wherein said flow controller is located on a side of said anchor opposite said cerebrospinal fluid inlet and said cerebrospinal fluid outlet.

8. The shunt of claim 1 wherein said flow controller is adapted to control flow rate of cerebrospinal fluid between said cerebrospinal fluid inlet and said cerebrospinal fluid outlet.

9. The shunt of claim 1 wherein said flow controller is adapted to be pressure sensitive and to adjust flow control responsive to pressure.

10. The shunt of claim 9 wherein said flow controller is manually adjustable to set a degree of flow control between said cerebrospinal fluid inlet and said cerebrospinal fluid outlet.

11. The shunt of claim 10 wherein said flow controller includes a control element having a cylindrical surface with threads thereon oriented about a central axis of a body to which said control element is threadably attached, said body containing said walled fluid pathway, said cerebrospinal fluid inlet and said cerebrospinal fluid outlet together in a rigid fashion;
   wherein said control element is adapted to be rotated relative to said housing through interaction of said threads on said control element with complemental threads on said body, and a first end of said control element adapted to block varying portions of said walled fluid pathway between said cerebrospinal fluid inlet and said cerebrospinal fluid outlet depending on a position of said control element on a second end opposite said first end which is adapted to receive a torque applying tool thereon, such that said control element can be rotated by a torque applying tool external to said body to adjust position of said control element to adjust flow rate of cerebrospinal fluid moving past said control element.

12. The shunt of claim 1 wherein said anchor includes a cannulated bolt and a hollow core and with portions of said walled fluid pathway adjacent both said cerebrospinal fluid inlet and said cerebrospinal fluid outlet located within said hollow interior of said cannulated bolt.

13. The shunt of claim 12 wherein said cannulated bolt includes a flange at an end of said cannulated bolt opposite a tip, said cerebrospinal fluid inlet located closer to said tip of said cannulated bolt than said cerebrospinal fluid outlet, said cerebrospinal fluid outlet located on a side of said flange common with said cerebrospinal fluid inlet, said cerebrospinal fluid inlet located a fixed distance away from said flange, such that when said flange abuts a supporting anatomical structure, the cerebrospinal fluid inlet will have extended a fixed distance away from the supporting anatomical structure.

14. A method for shunting fluid from a subarachnoid space of a spine to an epidural space of the spine, the method including the steps of:
providing a walled fluid pathway extending between a cerebrospinal fluid inlet and a cerebrospinal fluid outlet;
positioning the cerebrospinal fluid inlet in the subarachnoid space;
positioning the cerebrospinal fluid outlet in the epidural space; and
anchoring the walled fluid pathway to an anatomical structure proximate to the spine with the cerebrospinal fluid inlet and the cerebrospinal fluid outlet both on a common side of the anatomical structure.

15. The method of claim 14 including the further step of controlling flow between said cerebrospinal fluid inlet and said cerebrospinal fluid outlet.

16. The method of claim 15 wherein said controlling step includes the step of adjusting flow between said cerebrospinal fluid inlet and said cerebrospinal fluid outlet responsive to cerebrospinal fluid pressure.

17. The method of claim 15 wherein said controlling step includes the step of controlling a flow rate of cerebrospinal fluid between the cerebrospinal fluid inlet and the cerebrospinal fluid outlet.

18. The method of claim 15 wherein said controlling step includes the step of adjusting a flow rate of cerebrospinal fluid between the subarachnoid space and the epidural space.

19. The method of claim 14 including the further step of fixing a distance between the cerebrospinal fluid inlet and the cerebrospinal fluid outlet.

20. The method of claim 19 wherein said anchoring step includes the step of providing a cannulated bolt with the walled fluid pathway configured to have an elongate form routed through a hollow interior of the cannulated bolt, and with a flange on the bolt, with the flange located a fixed distance from the cerebrospinal fluid inlet and the cerebrospinal fluid outlet.

21. The method of claim 20 including the further step of configuring the walled fluid pathway as two concentric conduits passing through the hollow interior of the cannulated bolt, with a portion of the walled fluid pathway adjacent the cerebrospinal fluid inlet inboard of portions of the walled fluid pathway adjacent the cerebrospinal fluid outlet.

22. The method of claim 14 wherein said two positioning steps and said anchoring step occur simultaneously in a single linear insertion procedure.

23. The method of claim 22 including the further step of pre-forming a hole in the anatomical structure before the linear insertion procedure.

24. The method of claim 23 wherein the anatomical structure of said anchoring step is taken from the group of anatomical structures including a lamina of a spinal vertebra and a ligamentum flavum adjacent the spine.

25. A method for implanting a shunt, including the steps of:
providing a shunt having an elongate form with a centerline extending between a distal tip and a proximal end, with an anchor spaced from the distal tip and with an inlet and an outlet on a distal side of the anchor, the inlet and the outlet in fluid communication with each other inside the shunt;
selecting a desired position for the shunt;
aligning the centerline with the desired position and orientation for the shunt; and
axially advancing the shunt along the centerline until the shunt is positioned where desired.

26. The method of claim 25 wherein said selecting step includes selecting the desired position to be with the tip of the shunt in a subarachnoid space of a spine and with the anchor coupled to an anatomical structure outside of an epidural space of the spine.

27. The method of claim 26 wherein said anatomical structure of said selecting step is taken from the group of anatomical structures including a lamina of a spinal vertebra adjacent the spine and a ligamentum flavum adjacent the spine.

28. The method of claim 25 wherein said providing step includes providing the shunt to have the inlet closer to the tip than the outlet.

29. The method of claim 25 wherein said providing step includes the step of including a flange with the anchor and positioning the flange a fixed distance from the inlet and a fixed distance from the outlet, with a distance between the flange and the inlet sufficient to have the inlet within the subarachnoid space when the flange is adjacent the anatomical structure to which the anchor is secured, and with the outlet positioned within the epidural space.

30. The method of claim 25 wherein said providing step includes the step of having a flow controller between the inlet and the outlet.

* * * * *